United States Patent [19]

Chien et al.

[11] Patent Number: 5,116,471
[45] Date of Patent: May 26, 1992

[54] SYSTEM AND METHOD FOR IMPROVING SAMPLE CONCENTRATION IN CAPILLARY ELECTROPHORESIS

[75] Inventors: Ring-Ling Chien, San Jose; Dean S. Burgi, Palo Alto, both of Calif.

[73] Assignee: Varian Associates, Inc., Palo Alto, Calif.

[21] Appl. No.: 771,575

[22] Filed: Oct. 4, 1991

[51] Int. Cl.[5] .................. G01N 27/26; B01D 57/02
[52] U.S. Cl. ........................... 204/180.1; 204/299 R
[58] Field of Search ...................... 204/299 R, 180.1

[56] References Cited

PUBLICATIONS

Ruedi Aebersold & Hamish D. Morrison "Analysis of dilute peptide samples by capillary zone electrophoresis" *Journal of Chromatography* 516 (1990) 79–88.

Henk H. Lauer et al. "Analytical Aspects of an Automated Capillary Electrophoresis System" *LC–GC* vol. 6, No. 1 (1990) 34–46.

F. E. B. Mikkers, F. M. Everaerts, & Th. P. E. M. Verheggen "High–Performance Zone Electrophoresis" *Journal of Chromatography* 169 (1979) 11–20.

Dean S. Burgi & Ring-Ling Chien "Optimization in Sample Stacking for High-Performance Capillary Electrophoresis" Analytical Chemistry, vol. 63, No. 18 (1991) 2042–2047.

Moring, Stephen E., "Analytical Aspects of an Automated Capillary Electrophoresis System," *LC–GC*, vol. 8, No. 1 (1990) 34–46.

Jorgenson, James W. et al. "Capillary Zone Electrophoresis", *Science*, vol. 222, (1983), pp. 266–272.

Nielen, M. W. F., "Impact of Experimental Parameters on the Resolution of Positional Isomers of Aminobenzoic Acid in Capillary Zone Electrophoresis," *Journal of Chromatography*, 542 (1991) 173–183.

*Primary Examiner*—John Niebling
*Assistant Examiner*—John S. Starsiak, Jr.

[57] ABSTRACT

The method for improving sample concentration in capillary electrophoresis by extracting the sample buffer from the capillary column using the electro-osmotic flow while the sample components are stacked into the support buffer utilizes a system for this technique. The system has a separation column 11, sample introduction means 16 for injecting the sample solution, an injection detector means 20 for detecting the volume of injected sample solution, a separation detector means 21 for detecting the sample components, power supply means 17 for applying a high voltage along the separation column 11 for reversing the direction of the electro-osmotic flow thereby causing extraction of the sample buffer from the separation column and afterward providing the separation sample into its components.

33 Claims, 7 Drawing Sheets

WATER REMOVAL STEP

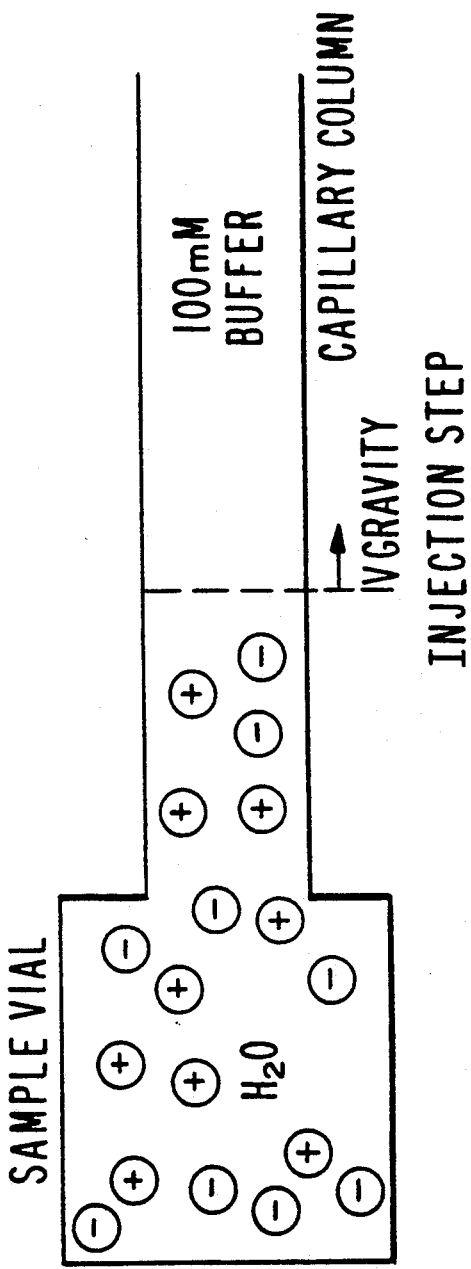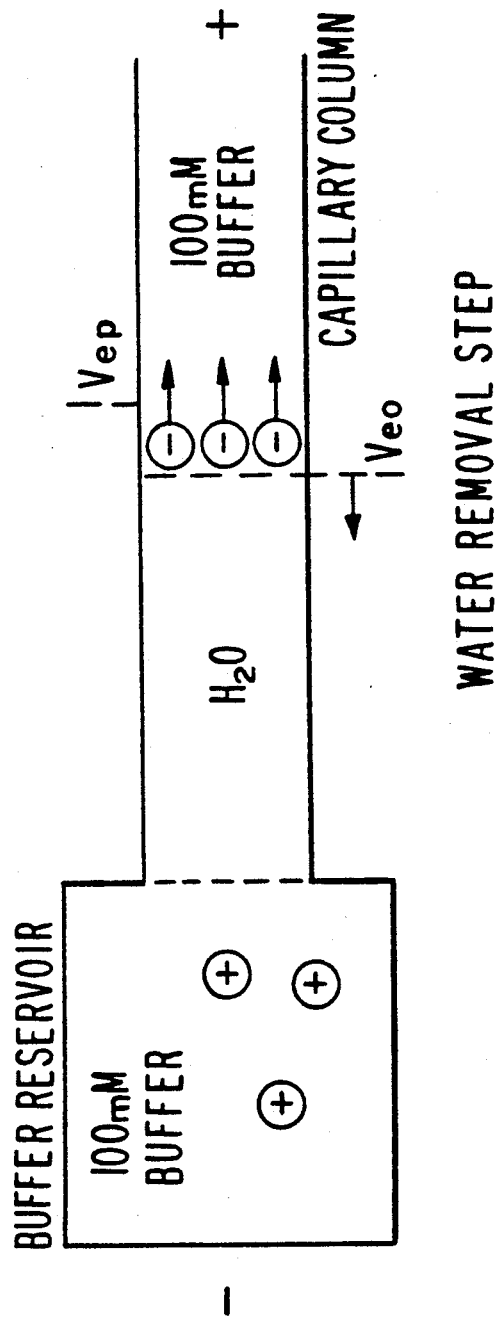
FIG. 2
FIG. 3

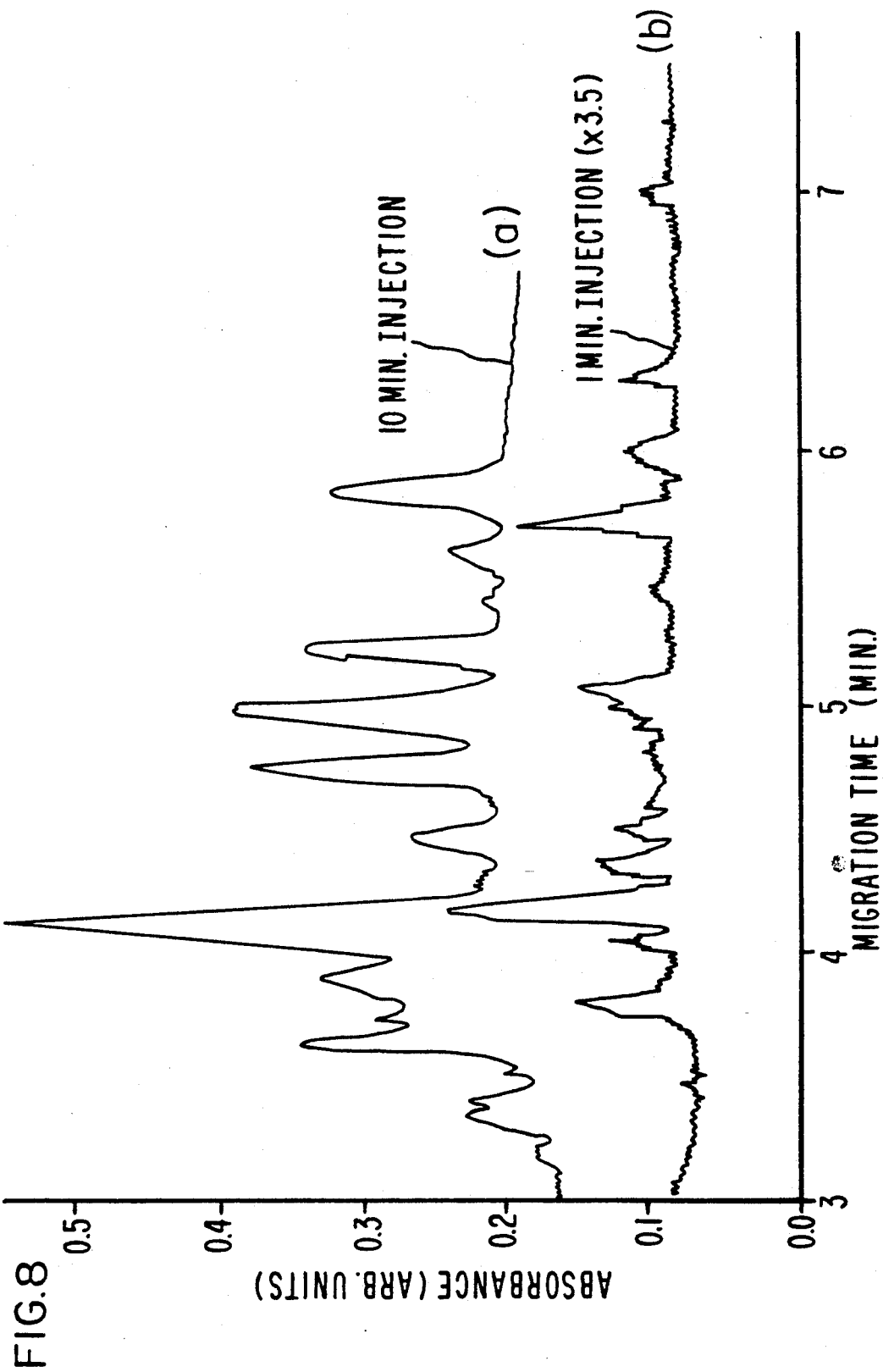

SYSTEM AND METHOD FOR IMPROVING SAMPLE CONCENTRATION IN CAPILLARY ELECTROPHORESIS

FIELD OF THE INVENTION

The present invention relates to capillary electrophoretic systems and methods for separation and detection of sample components inside a separation column, and more particularly to improved systems and methods for increasing detectability with a sample stacking technique in capillary electrophoresis.

BACKGROUND OF THE INVENTION

Capillary zone electrophoresis (CZE) is an efficient analytical separation technique which exploits the different mobilities of sample components in an electric field whereby the sample components are organized into zones in a capillary column.

A conventional CZE system widely used in practice comprises a buffer-filled capillary column with inlet and outlet ends disposed into two reservoirs, sample introduction means for injecting analyzed sample, on-column detector means for sensing the sample zones passing the detector, and high voltage means to apply a voltage to the capillary column causing the migration and separation of the sample components inside the column (see Jorgenson, J. W; and Lukacs, K. D., *Science*, 1983, v222, p. 266–272).

Using CZE for the analysis of very small sample volume creates a significant detection problem associated with the detection limit of conventional detectors. Along with the traditional technique of increasing the detection sensitivity of analyzed sample components through improvement of the detection systems, a different approach has been developed to increase sensitivity by concentrating the sample components into narrower zones in the capillary column. (Mikkers, F. E. P., Everaert, F. M.; Verheggen, Th P. E. M., *J. Chromatography* 1979, 169, 11). This on-column concentration technique sometimes called sample stacking, is obtained by applying a high voltage across a separation column which is filled with a plug of sample in a diluted buffer and surrounding which is a buffer having much higher conductivity than the sample plug.

A number of techniques using on-column concentration of sample ions at the boundary between a plug of sample in diluted buffer and the adjacent support buffer give the enhancement in detectability of the sample components. (Moring, S. E.; Colburn, T. C.; Grossman, P. D.; and Lauer, H. H.; *LC-GC*, 1990, 8,34; Aebersold, R. and Morrison, H. D.; *J. Chromatography* 1990, 516,79; Nielen, M. W. T.; *J. Chromatography* 1991, 542, 173).

DISADVANTAGE OF THE PRIOR ART

In the conventional CZE technique with on-column sample concentration, the attempts to significantly increase an injection sample volume lead to breakdown in resolution. Nielen injected sample volume up to 15 nl to obtain improvement of the concentration sensitivity. Better results in injecting up to 2% of the total capillary column volume were obtained by Moring, et al.

The limit in increasing the detectability of the above-described methods is the peak broadening mechanism caused by generation of laminar flow inside the capillary column. (Burgi, D. S.; and Chien, R. L.; *Anal. Chem.* 1991, 63, 2042). This laminar flow is generated from the mismatch of the local electro-osmotic mobilities and electric field strength between the sample buffer and the support buffer. The larger the sample volume introduced into the column, the broader the sample peaks will be. In general, a 10-fold increase in the amount of sample injected is obtainable before there is a loss in resolution due to laminar broadening. Another obstacle to a successful separation process of the sample ions is a very low strength of the electric field in the buffer bordering the long sample solution plug, and the much higher conductivity of the buffer compared to the sample plug. The electric field is low in the surrounding buffer because almost all of the electric field is dropped across the long sample plug, and that causes the electrophoretic velocity to decrease. This further limits the volume of sample solution injected into the column.

In addition, the systems for performing above methods do not provide the detection of the sample volume which allows rapid loading of the sample being introduced into the capillary column, that is very important for getting reproducability of this technique.

SUMMARY OF THE INVENTION

The foregoing disadvantage of prior art sample concentration methods and systems for performing capillary zone electrophoresis are overcome by the present invention. According to the invention, the water or diluted buffer is removed out of the column using the electro-osmotic flow while the sample components are stacked into the support buffer. The separation of the sample components is then performed in the column with minimum amount of laminar flow. This invention increases the amount of sample injected while retaining high resolution.

A system and method for high performance electrophoresis includes:

introducing consecutively a supporting buffer and a large plug of sample prepared in a diluted sample buffer which has a much lower concentration than the supporting buffer, into a separation column;

stacking sample ions at the boundary between the sample solution and the supporting buffer, while concurrently extracting the sample buffer from the separation column using the electro-osmotic flow caused due to application of reversed polarity high voltage along the separation column, separating sample ions according to their relative electrophoretic mobilities by applying a normal polarity high voltage along the separation column after removal of the sample buffer.

A system for performing the above described method including a separation column having inlet and outlet ends which are disposed respectively, in two buffer reservoirs containing support buffer; a sample introduction means for injecting sample prepared in sample buffer into the separation column, the sample buffer having a much lower concentration than the support buffer; an injection detector means for detecting the volume of injected sample solution; separation detector means for detecting the sample components at the outlet end of the separation column, and power supply means with electrodes which are disposed in the buffer reservoirs for applying the electric field gradient along the separation column and reversing the applied voltage polarity for reversing the direction of the electro-osmotic flow thereby causing extraction of the sample buffer from the separation column.

This technique is applicable for separation of either negative charged species or positive charged species since the direction of the electro-osmotic flow which pushes out the sample buffer from the capillary column depends on the charge of the capillary column walls.

BRIEF DESCRIPTION OF THE DRAWINGS

FIG. 2 is a schematic diagram of an injection into the capillary column of a sample diluted in sample buffer ($H_2O$).

FIG. 3 is a schematic diagram for extracting the sample buffer ($H_2O$) out of the capillary column.

FIG. 8 is a plot showing the comparison of a different duration for gravity injection with the sample buffer extraction.

PREFERRED EMBODIMENT OF THE INVENTION

Figure 1:
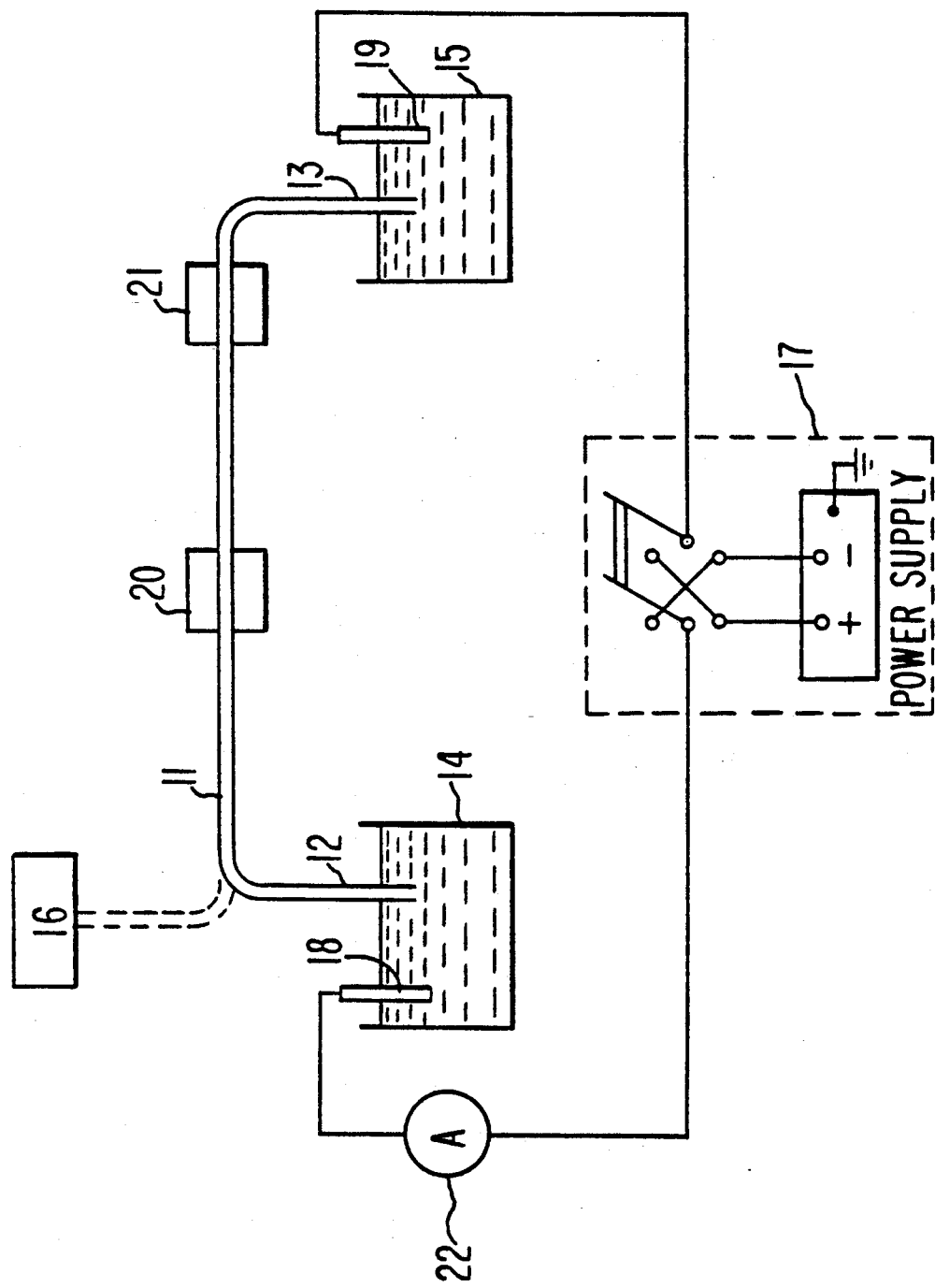
FIG. 1 is a system for high performance capillary electrophoresis according to the present invention.

An improved method of sample concentration in CZE was performed using a CZE system of the present invention and illustrated in FIG. 1. Referring to FIG. 1 a CZE system consists of a capillary column 11 with an inlet end 12 and an outlet end 13; the inlet end 12 and the outlet end 13 are dipped in the buffer reservoirs 14 and 15 containing support buffer; sample introduction means 16 for introducing sample solution inside the capillary column 11 through the inlet end 12; a power supply means 17 having electrode means 18 and 19 which is disposed in the reservoirs 14 and 15 respectively; an injection detector means 20 for detecting the volume of sample solution being introduced by sample introduction means 16 through inlet end 12 into the capillary column 11; separation detector means 21 for detecting the sample components at the outlet end 13 of the capillary column 11; ammeter 22 connected between power supply means 17 and either electrode means 18 or 19 for monitoring current flow through electrolytes within capillary column 11.

The support buffer is supplied from the reservoir 14 hydrodynamically to the capillary column 11 which is a 100 cm long, 50 $\mu$m ID, 365 $\mu$m OD fused capillary with a detector window at 35 cm from one end of the column (PolyMirco Technologies, Phoenix, AZ). Either end of the capillary column 11 might be used as the injection (inlet) side giving a detector window at 35 cm or 65 cm from the inlet end. The detector window was formed by burning off a 1 mm section of the outer polyamide coating.

Reservoir 15 at the outlet end 13 of the capillary column 11 collects the support buffer after filling the column. A high voltage is applied by power supply means 17 between the inlet end 12 and outlet end 13 of the capillary column 11 through electrode means 18 and 19, which are platinum wires preferably, for measuring the magnitude of electric current flow through the support buffer by ammeter 22.

Sample introduction means 16 is a syringe by which the sample solution is injected into the capillary column 11 until the injection detector means 20 responds to the sample solution passing through the window of the capillary column 11. This method allows ⅓ or ⅔ of the column to be filled rapidly depending on the location of the detector window to the inlet end of the capillary column. One can place the injection detection at the outlet end of the capillary column and fill the column completely up.

The alternative method of sample solution introduction is to position the sample solution vial 15 cm above the floor of the buffer reservoir 14. The inlet end 12 of the capillary column 11 is inserted into the vial and held there for 10 sec. to 20 min., which corresponds to plug lengths of 1 mm and 12 cm respectively. After injection, the inlet end 12 of the capillary column 11 is returned to the buffer reservoir 14. The volume of sample solution being introduced is detected by injection detector means 20 which is an UV absorbance detector, for example, a Varian 2550 (Walnut Creek, CA) with a 100 $\mu$m slit in a modified microcell holder. The wavelength for analysis is 265 nm.

While sample stacking is being performed, the sample buffer is pushed out into the buffer reservoir 14 by applying reversed polarity high voltage by the power supply means 17, between the inlet 12 and outlet ends 13 of the capillary column 11 through electrode means 18 and 19. The current flow level through sample solution and support buffer is monitored by ammeter 22 until its magnitude reaches within 1% of the current flow value of the support buffer.

For separation of the sample into its components, the polarity of the electrode means 18 and 19 is switched to normal, and high voltage is applied by power supply means 17 to the capillary column 11. The detection of the sample components at the outlet end 13 of the capillary 11 is provided by separation detector means 21 which is the same type of UV absorbance detection as the injection detector means.

SAMPLE CONCENTRATION PROCEDURES

The essence of keeping the high sample concentrated in sharp bands constitutes the method of extracting the sample buffer from the capillary column using electro-osmotic flow after the sample is stacked into the support buffer.

With a negatively charged silica capillary wall, the negative sample ions are stacked at the end of the plug of sample buffer and will follow the plug as it moves through the column under the applied electric field. For separation of positive sample ions, the charge on the silica capillary wall is made positive by adding Tetradecyltrimethylammonium bromide (TTAB) to the buffer, for changing the direction of the electro-osmotic flow.

The first step of the concentration technique is injection of the sample diluted in sample buffer which is shown schematically in FIG. 2. The sample buffer in this case is a pure water. The experiments were conducted with stock solution of $1.7 \times 10^{-4}$M PTH-Asp acid and $2.3 \times 10^{-4}$M PTH-Glu acid made up in HPLC grade distilled water (Aldrich, WI) then diluted to $3.4 \times 10^{-5}$M and $4.6 \times 10^{-5}$M respectively. The two positive species were $1.5 \times 10^{-4}$M PTH-Arg and $5.0 \times 10^{-5}$ M PTH-His. The support buffer was 100 mM sodium phosphate adjusted to pH of 6.6 or 100 mM MES/HIS adjusted to pH 6.1. All chemicals were purchased from Sigma (St. Louis, MO). Tryptic digest was done with 0.02 g of Cytachrome c (horse heart) and 0.001 g of trysin in 10 ml of water. The digest was kept at 37° C. for 28 hours, then diluted down to $5.0 \times 10^{-5}$ M with distilled water. The sample prepared in water was loaded into the capillary column by gravity injection.

Since the electrophoretic velocity of the ions inside the water plug is much faster than the bulk electro-osmotic velocity, application of high voltage with reversed polarity immediately after loading the sample causes extraction of the water plug (only) from the capillary column as shown in the FIG. 3. The negative ions are stacked into a thin zone on the back side of the sample plug.

Removal of the water plug from the capillary column is controlled by applying a high voltage with reverse polarity across the capillary column while monitoring the magnitude of the electric current flow through the sample solution and support buffer inside the column, and comparing it with the magnitude of the current flow through support buffer inside the column before injecting the sample solution inside the column.

When the current flow reaches 95% to 99% of the current flow of homogeneous systems, the voltage is disconnected. For further separation into components of the stacked sample ions, it is necessary to switch polarity of the electrodes to the normal polarity and apply high voltage having a comparable value to the high voltage being applied to the capillary column before sample solution injection.

Figure 4:
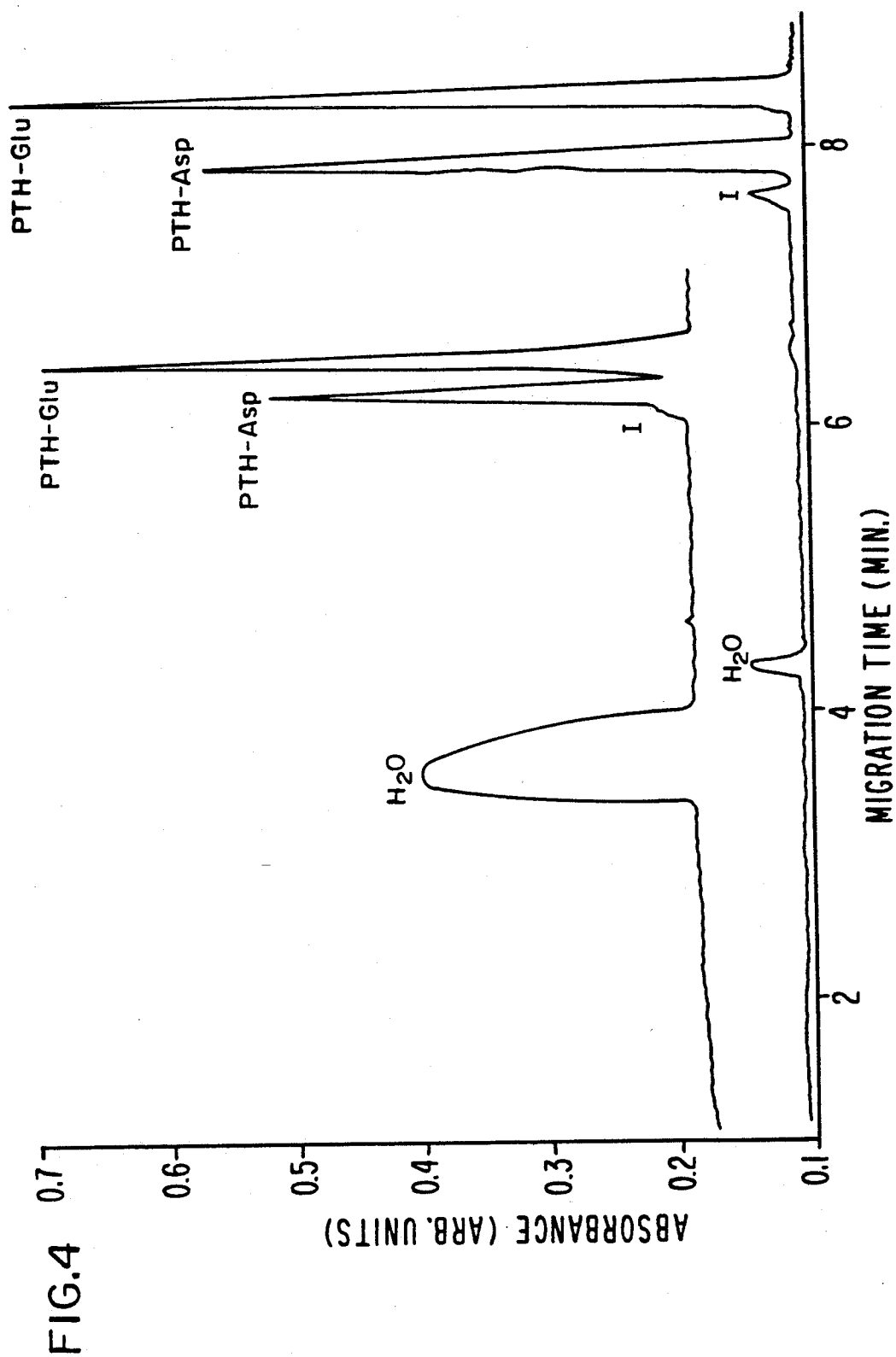
FIG. 4 is a plot showing the comparison of electropherograms with and without the sample buffer extraction in five minute injection.

The improvement in the separation of the sample obtained by the removal of the sample buffer (water) is shown in FIG. 4. The experiment was conducted under the following conditions: applied high voltage to the capillary column is on the order of 25 kV, and current flow through the support buffer inside the column is on the order of 225 $\mu$A for the phosphate buffer and 8 $\mu$A for the MES/HIS buffer. The electropherograms of a long sample plug (10 min. injection) with the water still in the column and with the water removed are shown in electropherograms (a) and (b), respectively. The resolution of the two analytes is much lower in electropherogram (a) because of the large amount of water in the column. The number of theoretical plates in electropherogram (a) are $2.5 \times 10^4$ and $2.3 \times 10^4$ for PTH-Asp and PTH-Glu respectively. The sample peaks are broadened due to a laminar flow generated by the long plug of sample buffer. The separation of the sample is not well resolved because the bulk electro-osmotic flow is increased and the electric field in the buffer portion of the column is reduced by the large amount of water. In constrast, the number of theoretical plates in electropherogram (b), where most of the water has been removed, are $4.2 \times 10^4$ and $4.5 \times 10^4$ respectively for the separation of PTH-Asp and PTH-Glu. All of the compounds in the sample plug are baseline resolved, the peak heights are greater, and the peak widths are narrower. Thus by removing the excess water after the sample is concentrated, we can improve the resolution and detectability of the sample.

Figure 5:
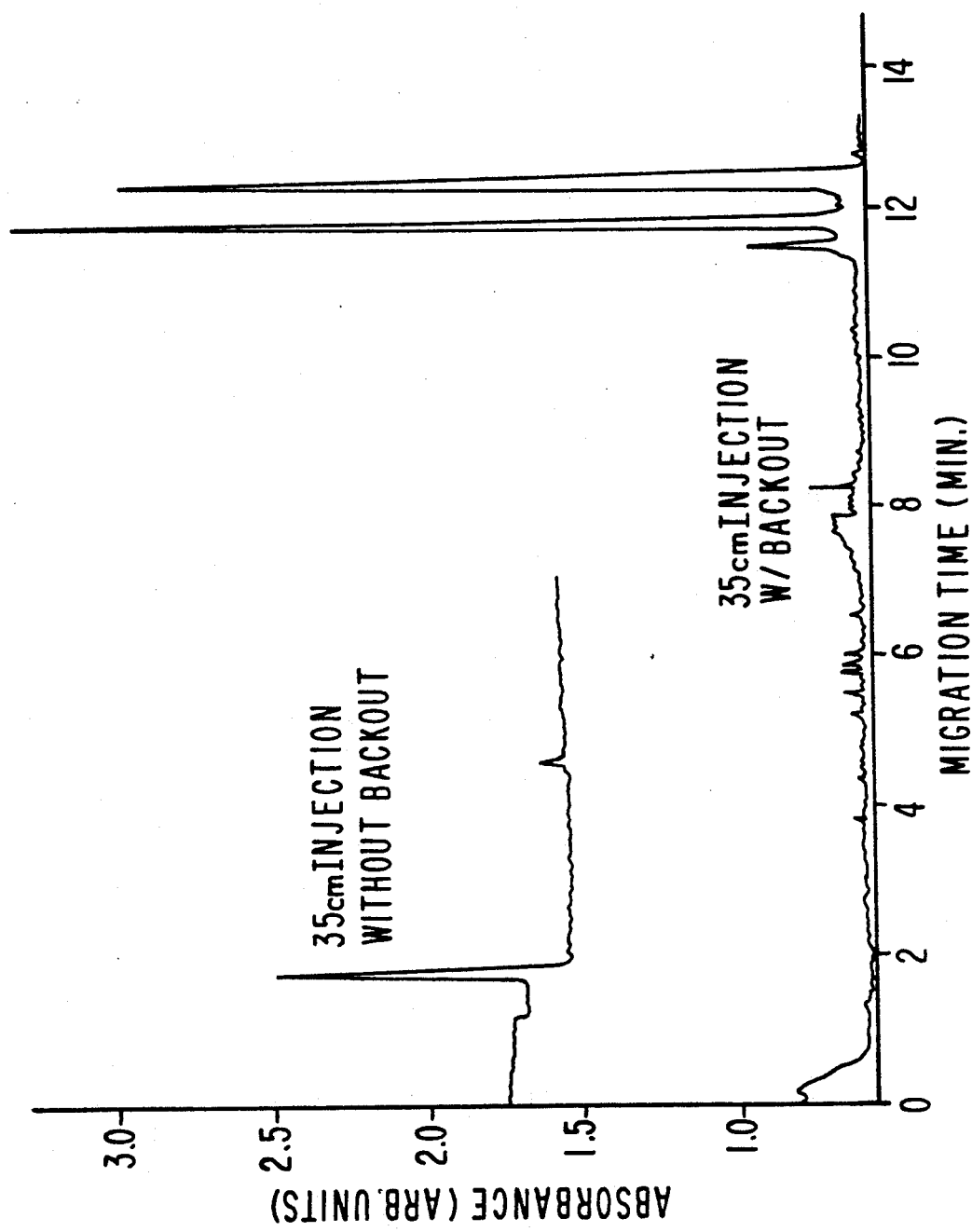
FIG. 5 is a plot showing the comparison of electropherograms with and without the sample buffer extraction for the length of sample plug is on the order of 35 cm.

FIG. 5 is a comparison between the injection of 35 cm of sample solution without and with the sample buffer removed from the column. As seen in the upper electropherogram, the negative ions stack up against the sample plug and since all of the electric field is dropped across the sample plug, the ions cannot separate themselves into discrete sample zones. The lower electropherogram shows the whole process of sample solution removal and ion separation. During the first 3 minutes of the process the sample buffer is removed. After the current reaches 99% of the support buffer current, the electrodes are switched. As seen, the remaining sample buffer passes the separation detector first, then the concentrated sample ions are detected with high resolution.

Figure 6:
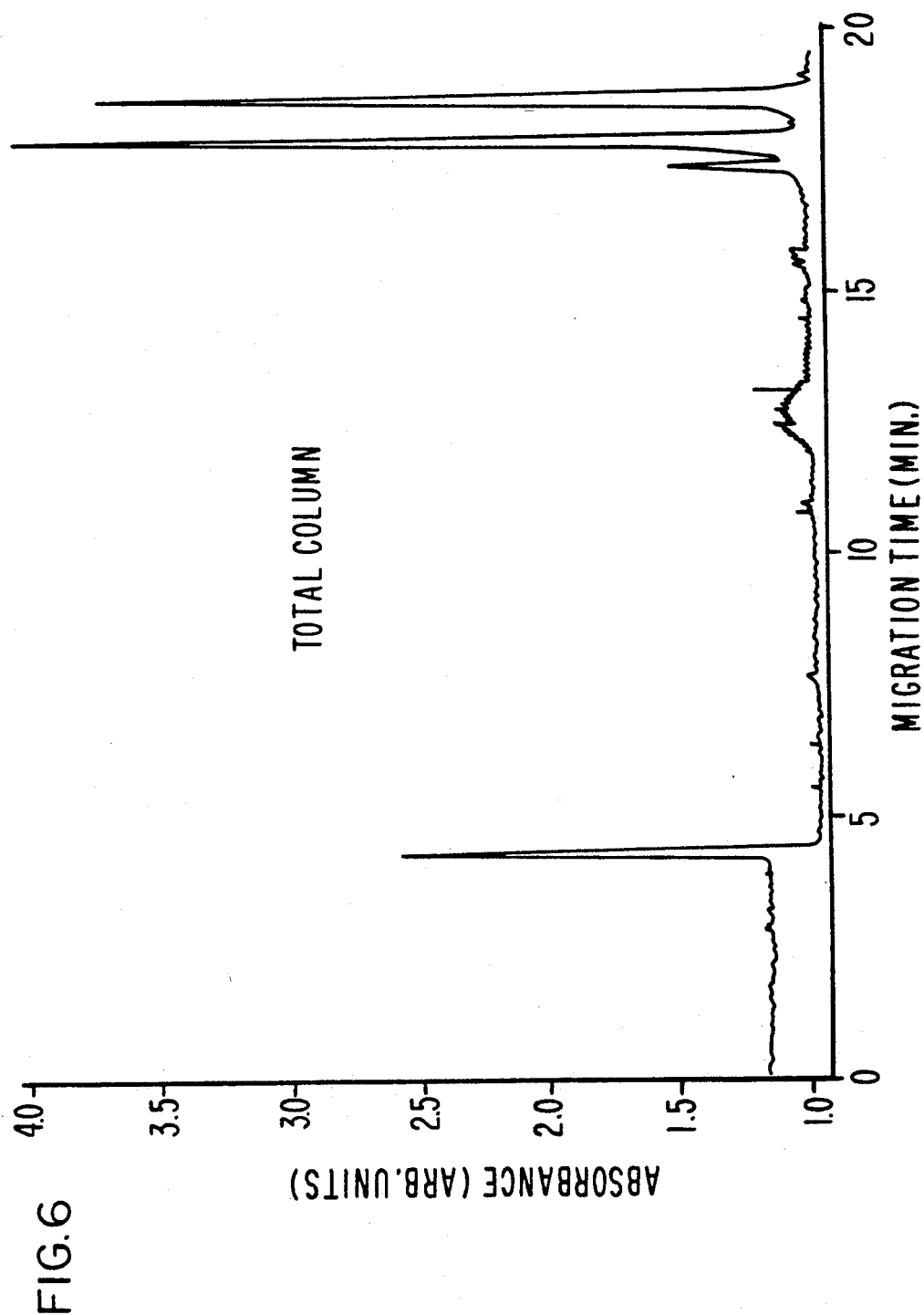
FIG. 6 is the electropherogram with the sample plug loading the entire separation column.

FIG. 6 is an electropherogram of an injection in which the entire column is filled with sample solution. The first 7 minutes is the removal of the sample buffer. After the current reaches 99% of the support buffer, the electrodes are switched. The sample buffer peak appears at 13 minutes and the sample ions appear later with high resolution. In other words, the sample ions in the entire column have been concentrated into very sharp zones.

Figure 7:
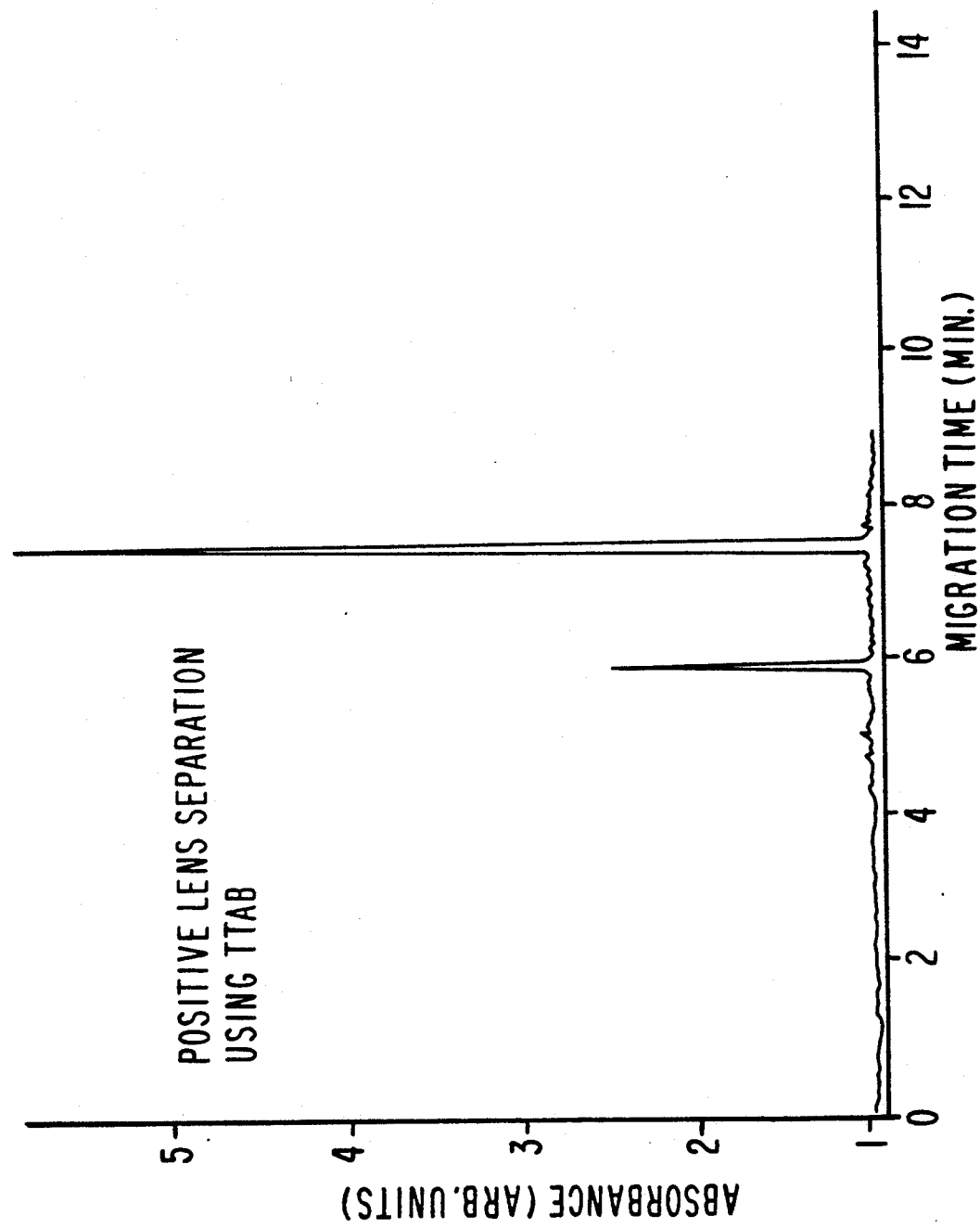
FIG. 7 is the electropherogram of positive charged ions separation.

FIG. 7 is an electropherogram of two positive species. The two sample ion are PTH-His and PTH-Arg respectively. The support buffer has 1 mM TTAB in it which reverses the electro-osmotic flow of the column.

A comparison of a tryptic digest of Cytachrome c at a 1 min. injection duration and a 10 min. injection duration with the water removed is shown in FIG. 8. One can see more peaks and greater peak heights using the concentrating method in the tryptic digest analysis; however, there is no one-to-one match of peaks between the two types of injection, possibly due to concentrating effects.

The experimental data demonstrate the improvement of the concentrating effect of sample stacking on the example of gravity injection. The sample buffer which causes a loss of resolution in the sample stacking technique is extracted by electro-osmotic flow from the separation column, and further separation of the concentrated sample zone proceeds under conventional electrophoretic conditions.

We claim:

1. A method for improving sample concentration in capillary electrophoresis comprising the steps of:

substantially filling a separation column with a first buffer;

measuring the magnitude of a current flow through said first buffer inside said separation column by applying a first voltage across said separation column for a period of time necessary for performing the measurement of said first current flow to determine the first current flow value;

obtaining sample solution by preparing a sample in a second buffer, said second buffer having concentration lower than said first buffer;

introducing a plug of said sample solution into said separation column adjacent to said first buffer;

concentrating ions of said sample at the boundary between said first buffer and said sample solution, and substantially extracting said second buffer from said separation column by applying a second voltage across said separation column and concurrently monitoring the magnitude of current flow through said sample solution and first buffer within said separation column, said second voltage having an opposite polarity to said first voltage;

applying a third voltage across said separation column for separating said sample into its components thereby providing a signal when each component is detected, said third voltage having opposite polarity to said second voltage.

2. The method of claim 1 wherein said first buffer has identical composition as said second buffer.

3. The method of claim 1 wherein said second buffer is pure water.

4. The method of claim 1 wherein said plug of said sample solution is introduced hydrodynamically into said separation column.

5. The method of claim 4 wherein said plug of said sample solution is introduced into said separation column until obtaining a response from said injection detector.

6. The method of claim 4 wherein a length of said plug of said sample solution is greater than 2% of a length of said separation column.

7. The method of claim 4 wherein said plug of said sample solution is introduced into said separation column until the length of said plug of said sample solution is comparable with the length of said separation column.

8. The method of claim 1 wherein said first voltage and said third voltage have a comparable value.

9. The method of claim 1 wherein step of substantially extracting said second buffer from said separation column comprises:
applying said second voltage to achieve a second current flow having an opposite direction to said first current flow, maintaining said second voltage until said second current flow increases to a selected value, said selected value less than said first current flow value.

10. The method of claim 9 wherein said second current flow is substantially 99% of said first current flow.

11. A capillary electrophoresis system comprising:
a separation column having inlet and outlet ends;
a support buffer within said separation column;
a sample introduction means for loading a plug of a sample solution into said separation column, said sample solution being a sample diluted in a sample buffer;
an injection detector means for detecting the volume of said sample diluted in said sample buffer being introduced in said separation column at said inlet end;
a separation detector means for detecting the sample components at the outlet end of said separation column;
a power supply means having electrode means to apply an electric field along said separation column for concentrating sample ions at the boundary between said support buffer and said sample solution within said separation column and for extraction of said sample buffer out of said column by switching the polarity of said electric field of said electrode means thereby translating said sample along said column for separating said sample into components thereof by again reversing the polarity of said electric field of said electrode means;
a measuring means for measuring the magnitude of electric current flow through said support buffer and said sample diluted in said sample buffer within said separation column.

12. The system of claim 11 wherein said separation column is a capillary tube.

13. The system of claim 12 further comprising a first and a second buffer reservoir for containing said support buffer wherein said electrode means of said power supply means are disposed to apply electric field along said capillary tube, said first and said second buffer reservoir are disposed at said inlet and said outlet ends of said capillary tube respectively.

14. The system of claim 11 wherein said measuring means is connected between said power supply means and any one of said electrode means.

15. The system of claim 1 wherein said injection detector is placed at a selected distance from said inlet end of said separation column for detecting the volume of the injected said sample solution.

16. The process for high performance capillary electrophoresis by increasing concentration of the positive charged ions of the sample comprising the steps of:
substantially filling a separation column with first buffer;
measuring the magnitude of a current flow through said first buffer inside said separation column by applying a first voltage along said separation column for a period of time necessary for performing the measurement of said first current flow to determine the first current flow value;
obtaining sample solution by preparing a sample in a second buffer, said second buffer having concentration lower than said first buffer;
introducing a plug of said sample solution into said separation column adjacent to said first buffer;
concentrating positive charged ions of the sample at the boundary between said first buffer and said sample solution, and substantially extracting said second buffer from said separation column by applying a second voltage along said separation column and concurrently monitoring the magnitude of current flow through said sample solution and first buffer within said separation column, said second voltage having an opposite polarity to said first voltage;
applying a third voltage along said separation column for separating said sample into its components thereby providing a signal when each component is detected, said third voltage having opposite polarity to said second voltage.

17. The process of claim 16 wherein said separation column is a capillary tube having silica walls;

18. The process of claim 16 wherein said second buffer having a modifier to charge said silica walls of said capillary tube positively.

19. The process of claim 18 wherein said modifier is cetyltrimethylammonium bromide.

20. The process of claim 16 wherein said first buffer has identical composition as said second buffer.

21. The process of claim 16 wherein said second buffer is pure water.

22. The process of claim 16 wherein said plug of said sample solution is introduced hydrodynamically into said separation column.

23. The process of claim 16 wherein said first voltage and said third voltage have a comparable value.

24. The process of claim 16 wherein step of substantially extracting said second buffer from said separation column comprises:
applying said second voltage to achieve a second current flow having an opposite direction to said first current flow, maintaining said second voltage until said second current flow increases to a selected value, said selected value less than said first current flow value.

25. The process of claim 24 wherein said second current flow is substantially 99% of said first current flow.

26. The process for high performance capillary electrophoresis by increasing concentration of the negative charged ions of the sample comprising the steps of:
substantially filling a separation column with first buffer,
measuring the magnitude of a current flow through said first buffer inside said separation column by applying a first voltage along said separation column for a period of time necessary for performing the measurement of said first current flow to determine the first current flow value;
obtaining sample solution by preparing a sample in a second buffer, said second buffer having concentration lower than said first buffer;
injecting a plug of said sample solution into said separation column adjacent to said first buffer;
concentrating negative charged ions of the sample at the boundary between said first buffer and said sample solution and substantially extracting said second buffer from said separation column by applying a second voltage along said separation column and concurrently monitoring the magnitude of current flow through said sample solution and first buffer within said separation column, said second voltage having an opposite polarity to said first voltage;
applying a third voltage along said separation column for separating said sample into its components thereby providing a signal when each component is detected, said third voltage having opposite polarity to said second voltage.

27. The process of claim 26 wherein said separation column is a capillary tube having silica walls.

28. The process of claim 26 wherein said first buffer has identical composition as said second buffer.

29. The process of claim 26 wherein said second buffer is pure water.

30. The process of claim 26 wherein said plug of said sample solution is introduced hydrodynamically into said separation column;

31. The process of claim 26 wherein said first voltage and said third voltage have a comparable value.

32. The process of claim 26 wherein step of substantially extracting said second buffer from said separation column comprises:
applying said second voltage to achieve a second current flow having an opposite direction to said first current flow, maintaining said second voltage until said second current flow increases to a selected value, said selected value less than said first current flow value.

33. The process of claim 32 wherein said second current flow is substantially 99% of said first current flow.

* * * * *